United States Patent [19]
Grohe et al.
[11] Patent Number: 4,563,459
[45] Date of Patent: Jan. 7, 1986

[54] MICROBICIDAL AGENTS BASED ON QUINOLONECARBOXYLIC ACID

[75] Inventors: Klaus Grohe, Odenthal; Uwe Petersen, Leverkusen; Karl-Heinz Kuck, Langenfeld, all of Fed. Rep. of Germany

[73] Assignee: Bayer Aktiengesellschaft, Leverkusen, Fed. Rep. of Germany

[21] Appl. No.: 561,441

[22] Filed: Dec. 14, 1983

[30] Foreign Application Priority Data

Dec. 29, 1982 [DE] Fed. Rep. of Germany ....... 3248507

[51] Int. Cl.[4] ...................... A01N 43/58; A01N 43/60; A01N 55/02; A01N 43/84

[52] U.S. Cl. .................................... 514/254; 514/187; 514/222; 514/233; 514/312

[58] Field of Search ......................... 424/250; 514/254

[56] References Cited

U.S. PATENT DOCUMENTS

| | | | |
|---|---|---|---|
| 4,146,625 | 3/1979 | Lee | 424/258 |
| 4,146,719 | 3/1979 | Irikura | 424/250 |

FOREIGN PATENT DOCUMENTS

| | | |
|---|---|---|
| 0000203 | 1/1979 | European Pat. Off. . |
| 0049355 | 4/1982 | European Pat. Off. . |
| 2804097 | 11/1978 | Fed. Rep. of Germany . |
| 3007006 | 8/1980 | Fed. Rep. of Germany . |
| 3033157 | 4/1982 | Fed. Rep. of Germany . |

OTHER PUBLICATIONS

Chemical Abstracts, 99: 53790h, (1983).
Chemical Abstracts, 97: 55793u, (1982).

*Primary Examiner*—Jerome D. Goldberg
*Assistant Examiner*—John M. Kilcoyne
*Attorney, Agent, or Firm*—Sprung Horn Kramer & Woods

[57] ABSTRACT

Combating microorganisms, particularly in agriculture, with a 1-cyclopropyl-1,4-dihydro-4-oxo-quinolinecarboxylic acid of the formula

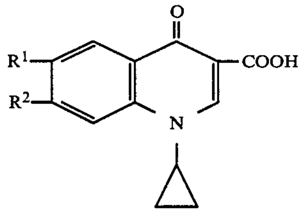

in which
$R^1$ is hydrogen, fluorine, chlorine, bromine or nitro,
$R^2$ is hydrogen, chlorine, fluorine or the group

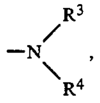

particularly a 4-piperazinyl radical, or an acid addition, alkali metal, alkaline earth metal or heavy metal salt thereof which is tolerated by plants, or a hydrate thereof. Some of the compounds are known.

6 Claims, No Drawings

MICROBICIDAL AGENTS BASED ON QUINOLONECARBOXYLIC ACID

The invention relates to the use of 1-cyclopropyl-1,4-dihydro-4-oxo-3-quinolinecarboxylic acids, some of which are known, as microbicides.

Certain 1-cyclopropyl-1,4-dihydro-4-oxo-3-quinolinecarboxylic acids, such as, for example, 1-cyclopropyl-6-fluoro-1,4-dihydro-4-oxo-7-(1-piperazinyl)-3-quinolinecarboxylic acid, are already known (compare European Pat. No. 49,355). Nothing is known of a microbicidal action in the field of plant protection, only their use in the field of drugs.

It has also been disclosed that certain quinolonecarboxylic acid derivatives have a phytobactericidal activity. Thus, 7-chloro-1-ethyl-6-fluoro-1,4-dihydro-4-oxo-3-quinolinecarboxylic acid displays a bactericidal action specifically against *Erwinia amylovora* (fireblight of fruit trees) (compare European Patent Application No. 0,203). However, the activity is not always satisfactory when low concentrations are applied.

It has been found that the 1-cyclopropyl-1,4-dihydro-4-oxo-3-quinolinecarboxylic acids, some of which are known, of the formula (I)

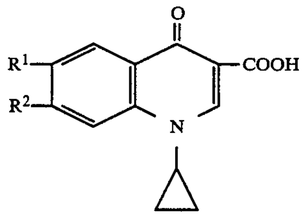

(I)

in which $R^1$ represents hydrogen, fluorine, chlorine, bromine or nitro and $R^2$ represents hydrogen, chlorine, fluorine or the group

wherein $R^3$ and $R^4$ are identical or different and represent alkyl which has 1 to 4 carbon atoms and is optionally substituted by hydroxyl, or $R^3$ and $R^4$, together with the nitrogen atom on which they are positioned, form a 5-membered or 6-membered, saturated or partially unsaturated heterocyclic ring which is optionally mono- or poly-substituted by identical or different substituents and can optionally contain other heteroatoms, such as oxygen, sulphur or an SO, $SO_2$ or $NR^5$ group. Substituents of the heterocyclic radicals which may be mentioned are: alkyl with 1 to 6 carbon atoms, alkenyl with 2 to 6 carbon atoms, phenyl and hydroxyl, and $R^5$ represents hydrogen, alkyl which has 1 to 12 carbon atoms and is optionally mono- or poly-substituted by identical or different substituents from the group comprising hydroxyl and alkoxy with 1 to 4 carbon atoms, or represents phenylalkyl which has 1 to 3 carbon atoms in the alkyl part and is optionally substituted by nitro, amino or the group $-O-CH_2-O-$, or represents phenyl which is optionally mono- or poly-substituted by identical or different substituents from the group comprising halogen, halogenoalkyl with 1 or 2 carbon atoms and with up to 5 halogen atoms, hydroxyl, alkoxy with 1 to 3 carbon atoms and the group $-O-CH_2-O-$, or represents heteroaryl or the grouping

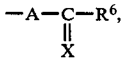

wherein

A represents an optionally substituted alkylene chain with 1 to 4 carbon atoms, $R^6$ represents hydrogen, alkyl with 1 to 6 carbon atoms, or phenyl which is optionally mono- or poly-substituted by hydroxyl, halogen or alkoxy and X represents oxygen or the grouping $=NOR'$, $=N-NH-R''$ or $(OR''')_2$, wherein $R'$ represents hydrogen, alkyl with 1 to 6 carbon atoms, cycloalkyl with 5 or 6 carbon atoms, benzyl, chlorobenzyl or tetrahydropyranyl, $R''$ represents methyl, phenyl, carbamoyl or thiocarbamoyl and $R'''$ represents methyl or ethyl, or $(OR''')_2$ represents

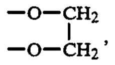

and acid addition, alkali metal, alkaline earth metal and heavy metal salts thereof which are tolerated by plants, and where relevant the hydrates, have powerful microbicidal properties in the field of plant protection.

Surprisingly, the 1-cyclopropyl-1,4-dihydro-4-oxo-3-quinolinecarboxylic acids of the formula I exhibit a substantially broader and better action, especially against phtyopathogenic bacteria, than the comparable quinolonecarboxylic acids known from the prior art, such as, for example, 7-chloro-1,4-dihydro-1-ethyl-6-fluoro-4-oxo-3-quinolinecarboxylic acid, which, from the point of view of their action, are chemically very closely related compounds.

The new use of the active compounds thus represents an enrichment of the art.

Formula (I) provides a definition of the compounds which can be used according to the invention. Preferably, in this formula, $R^1$ represents hydrogen, fluorine, chlorine or nitro and $R^2$ represents chlorine, fluorine or the group

wherein $R^3$ and $R^4$ are identical or different and represent alkyl with 1 to 3 carbon atoms or alkyl which has 2 or 3 carbon atoms and is monosubstituted by hydroxyl, or R³ and R⁴, together with the nitrogen atom on which they are positioned, represent 1-pyrrolidinyl, 1-piperidinyl, 1,2,3,6-tetrahydro-1-pyridyl, 4-morpholinyl, 4-thiomorpholinyl or 1,1-dioxo-4-thiomorpholinyl, each of which is optionally mono-, di- or tri-substituted by alkyl with 1 to 4 carbon atoms, alkenyl with 2 to 4 carbon atoms, phenyl or hydroxyl, or $R^3$ and $R^4$, together with the nitrogen atom on which they are positioned, form the heterocyclic radical

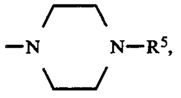

which can be substituted as described above, and $R^5$ is hydrogen, alkyl with 1 to 12 carbon atoms, alkyl which has 1 to 4 carbon atoms and is monosubstituted by hydroxyl, alkyl which has 1 to 4 carbon atoms and is monosubstituted by methoxy, phenyl which is optionally mono-, di- or trisubstituted by hydroxyl, alkoxy with 1 or 2 carbon atoms, trifluoromethyl, fluorine or dioxymethylene, pyridyl, pyrimidinyl, phenalkyl which has 1 or 2 carbon atoms in the alkyl part and is optionally substituted by dioxymethylene, or the grouping

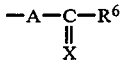

wherein

A is an alkylene chain with 1 to 3 carbon atoms, $R^6$ is hydrogen, alkyl with 1 to 4 carbon atoms, or represents phenyl which is optionally mono-, di- or trisubstituted by identical or different substituents from the group comprising hydroxyl, fluorine, chlorine and methoxy and X is oxygen or the grouping =NOR', =N—NHR'' or $(OR''')_2$, wherein R' is alkyl with 1 to 3 carbon atoms, benzyl or tetrahydropyranyl, R'' is methyl, carbamoyl or thiocarbamoyl and R''' is methyl or ethyl, or $(OR''')_2$ for

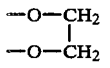

and acid addition, alkali metal, alkaline earth metal or heavy metal salts thereof which are tolerated by plants, and the hydrates.

The following compounds may be mentioned as examples, in addition to the compounds mentioned in the preparation examples: 1-cyclopropyl-6,7-difluoro-1,4-dihydro-4-oxo-3-quinolinecarboxylic acid, 1-cyclopropyl-6-chloro-1,4-dihydro-4-oxo-7-(4-β-hydroxyethyl-1-piperazinyl)-3-quinolinecarboxylic acid, 1-cyclopropyl-6-chloro-1,4-dihydro-4-oxo-7-(4-morpholinyl)-3-quinolinecarboxylic acid, 1-cyclopropyl-6-chloro-1,4-dihydro-4-oxo-7-(4-methyl-1-piperazinyl)-3-quinolinecarboxylic acid, 1-cyclopropyl-6-fluoro-1,4-dihydro-4-oxo-7-(2,5-dimethyl-1-piperazinyl)-3-quinolinecarboxylic acid, 1-cyclopropyl-6-fluoro-1,4-dihydro-4-oxo-7-(2,4,5-trimethyl-1-piperazinyl)-3-quinolinecarboxylic acid, 1-cyclopropyl-6-fluoro-1,4-dihydro-4-oxo-7-(3,4,5-trimethyl-1-piperazinyl)-3-quinolinecarboxylic acid, 1-cyclopropyl-6-fluoro-1,4-dihydro-4-oxo-7-(4-ethyl-3,5-dimethyl-1-piperazinyl)-3-quinolinecarboxylic acid, 1-cyclopropyl-6-fluoro-1,4-dihydro-4-oxo-7-(3,4-di-ethyl-1-piperazinyl)-3-quinolinecarboxylic acid, 1-cyclopropyl-6-fluoro-1,4-dihydro-4-oxo-7-(3-n-propyl-1-piperazinyl)-3-quinolinecarboxylic acid, 1-cyclopropyl-6-fluoro-1,4-dihydro-4-oxo-7-(3-isopropyl-1-piperazinyl)-3-quinolinecarboxylic acid, 1-cyclopropyl-6-fluoro-1,4-dihydro-4-oxo-7-(4-sec.-butyl-3-methyl-1-piperazinyl)-3-quinolinecarboxylic acid and 1-cyclopropyl-6-chloro-1,4-dihydro-4-oxo-7-(4-tert.-butyl-3-methyl-1-piperazinyl)-3-quinolinecarboxylic acid, and, where appropriate, their acid addition, alkali metal, alkaline earth metal or heavy metal salts and hydrates which are tolerated by plants.

If appropriate, the resulting compounds of the formula I according to the invention can be converted into a salt with an organic or inorganic acid. Examples of suitable acids for salt formation are the hydrogen halide acids, such as hydrochloric acid, hydrobromic acid and hydriodic acid, sulphuric acid, acetic acid, citric acid, ascorbic acid, methanesulphonic acid and benzenesulphonic acid. Preferred suitable alkali metal or alkaline earth metal salts are the sodium, potassium, calcium and magnesium salts, and preferred suitable heavy metal salts are the copper, zinc and manganese salts.

Acid salts of the compounds of the formula (I) can be obtained in a simple manner by customary salt formation methods, for example by dissolving a compound in a suitable inert solvent and adding one of the abovementioned acids, and they can be isolated in a known manner, for example by filtration, and if appropriate purified by washing with an inert organic solvent.

Specific examples of the compounds according to the invention are new, but they can be prepared by processes which are known in principle. In this context, compare the preparation examples.

The active compounds according to the invention exhibit a powerful microbicidal action and can be employed in practice for combating undesired microorganisms. The active compounds are suitable for use as plant protection agents.

Thus, for example, bactericidal agents are employed in plant protection for combating Pseudomonadaceae, Rhizobiaceae, Enterobacteriaceae, Corynebacteriaceae and Streptomycetaceae.

The good toleration, by plants, of the active compounds in the concentrations necessary for combating plant diseases permits treatment of above-ground parts of plants, of vegetative propagation stock and seed, and of the soil.

The compounds according to the invention are particularly active against bacteria of the genera Xanthomonas, for example against *Xanthomonas oryzae*, Pseudomonas, for example against *Pseudomonas lachrymans* and Erwinia, for example against *Erwinia carotovora* var. *atroseptica*.

When applied in appropriate concentrations, some of the compounds also have a fungicidal action. The actions against Oomycetes and against scab fungi (Venturia) and the protective and systemic action against *Pyricularia oryzae* may be mentioned in particular.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or form-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The known compound shown below is used as a comparison substance in the examples which follow.

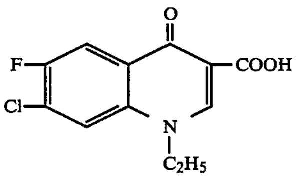

(A)

7-Chloro-1-ethyl-6-fluoro-1,4-dihydro-4-oxo-3-quinolinecarboxylic acid.

EXAMPLE A

Xanthomonas oryzae test/bacteriosis/rice protective

Solvent: 48.5 parts by weight of dimethylformamide
Emulsifier: 1.5 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After 48 hours, the plants are inoculated with an aqueous suspension of Xanthomonas oryzae by pricking the leaves. After incubation at 100% relative atmospheric humidity for 48 hours, the plants remain in a greenhouse at 24° to 26° C. and 70 to 80% relative atmospheric humidity for 10 days until they are evaluated.

The results obtained are as follows:

TABLE A
*Xanthomonas oryzae* test/bacteriosis/rice protective
| Active compounds | Active compound concentration in % | Disease infestation in % of the untreated control |
|---|---|---|
| 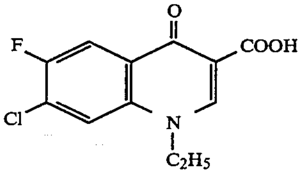 (known) | 0.025 | 75 |
| 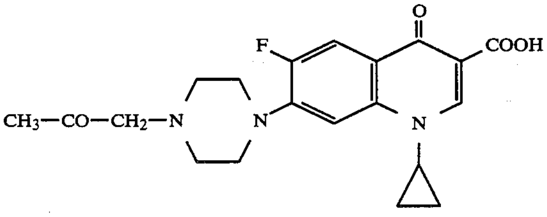 | 0.025 | 20 |
| 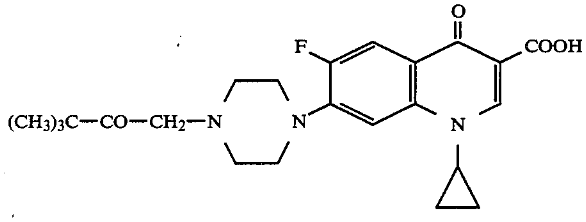 | 0.025 | 37.5 |
| 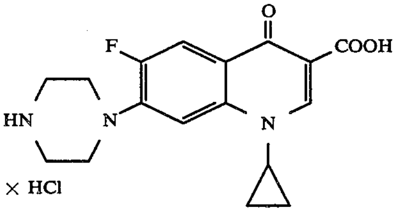 × HCl | 0.025 | 20 |
| 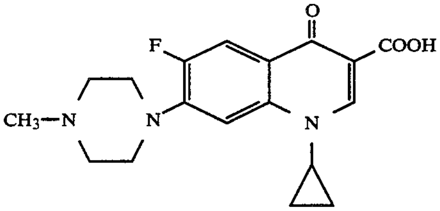 | 0.025 | 25 |
| 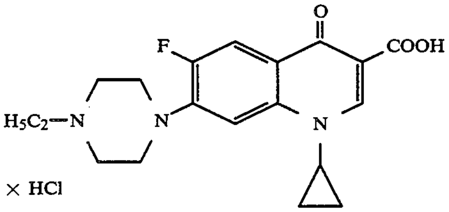 × HCl | 0.025 | 25 |

TABLE A-continued

*Xanthomonas oryzae* test/bacteriosis/rice protective

| Active compounds | Active compound concentration in % | Disease infestation in % of the untreated control |
|---|---|---|
| 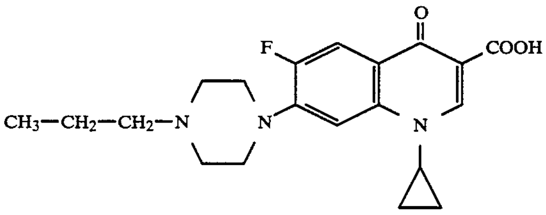 | 0.025 | 25 |
| 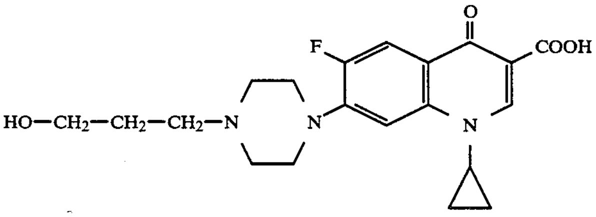 | 0.025 | 25 |
| 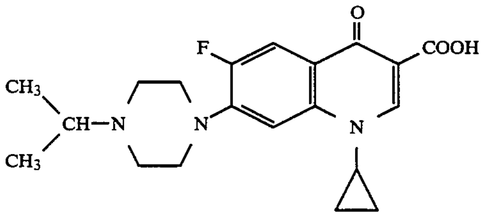 | 0.025 | 25 |

EXAMPLE B

Xanthomonas oryzae test/bacteriosis/rice

Solvent: 48.5 parts by weight of dimethylformamide
Emulsifier: 1.5 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for systemic properties, standard soil in which young plants have been grown is watered with 100 ml of the preparation of active compound. 3 days after the treatment, the plants are inoculated with an aqueous suspension of Xanthomonas oryzae by pricking. Thereafter, the plants remain in a greenhouse at 24 to 26° C. and 70 to 80% relative atmospheric humidity for 14 days until they are evaluated.

The results obtained are as follows:

TABLE B

*Xanthomonas oryzae* test/bacteriosis/rice systemic

| Active compounds | Amount applied in mg of active compound per 100 $cm^2$ | Disease infestation in % of the untreated control |
|---|---|---|
| 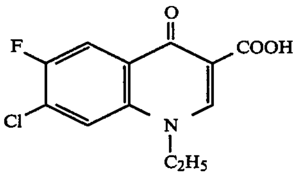 (known) | 10 | 25 |

TABLE B-continued

*Xanthomonas oryzae* test/bacteriosis/rice systemic

| Active compounds | Amount applied in mg of active compound per 100 $cm^2$ | Disease infestation in % of the untreated control |
|---|---|---|
| 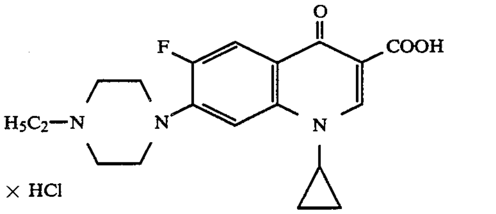 × HCl | 10 | 6 |
| 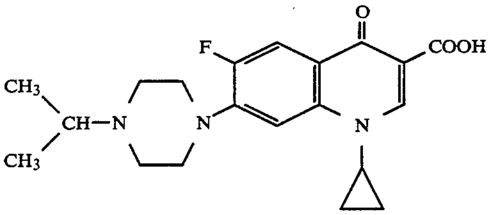 | 10 | 12 |
| 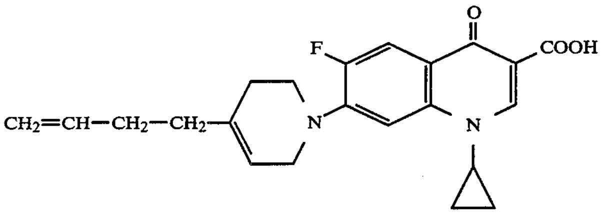 | 10 | 12 |

EXAMPLE C

Agar plate test

Nutrient medium used 15 parts by weight of agar-agar
10 parts by weight of sucrose
8 parts by weight of casein hydrolyzate
4 parts by weight of yeast extract
2 parts by weight of dipotassium hydrogen phosphate
0.3 parts by weight of magnesium phosphate are dissolved in 1,000 ml of distilled water and the solution is kept in an autoclave at 121° C. for 30 minutes.

Solvent: 10 parts by weight of dimethylformamide

Ratio of the amounts of solvent to nutrient medium: 0.2:99.8

To produce a suitable preparation of active compound, 1 part by weight of active compound is mixed with the stated amount of solvent.

The concentrate is thoroughly mixed, in the stated proportion, with the liquid nutrient medium and the mixture is then poured into Petri dishes.

When the nutrient medium has cooled and solidified, the plates are inoculated with the following microorganisms and are incubated at about 28° C.:

Evaluation is carried out after 2 days, the inhibition of growth being used as a measure of the action of the products.

The results obtained are as follows:

TABLE C

Agar plate test

| Active compounds | Active compound concentration ppm | Growth in figures of rating (1 = growth, 9 = control) Microorganisms: *Agrobacterium tumefaciens* | *Corynebacterium michiganense* | *Erwinia carotovora* var. *atroseptica* | *Erwinia mangiferae* |
|---|---|---|---|---|---|
| 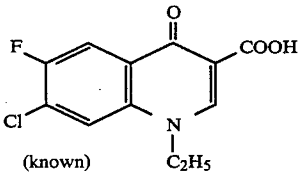 (known) | 50 | 5 | 5 | 2 | 7 |

TABLE C-continued
Agar plate test
| Active compounds | Active compound concentration ppm | Growth in figures of rating (1 = growth, 9 = control) Microorganisms: *Agrobacterium tumefaciens* | *Corynebacterium michiganense* | *Erwinia carotovora* var. *atroseptica* | *Erwinia mangiferae* |
|---|---|---|---|---|---|
| 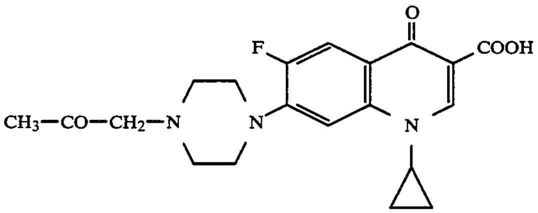 | 50 | 2 | 1 | 1 | 1 |
| 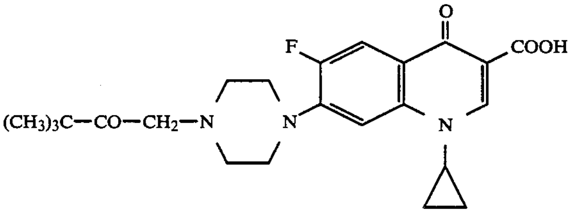 | 50 | 2 | 1 | 1 | 1 |
| 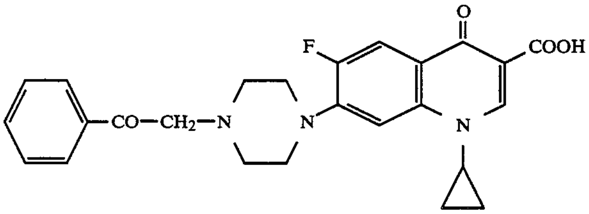 | 50 | 2 | 1 | 1 | 1 |
| 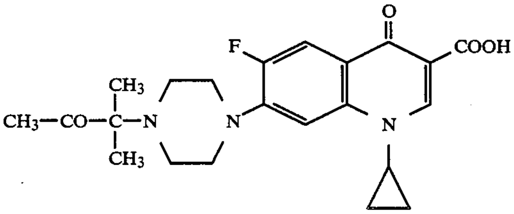 | 50 | 2 | 1 | 1 | 1 |
| 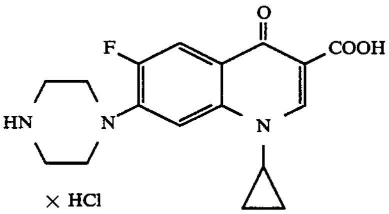 | 50 | 2 | 2 | 1 | 1 |
| 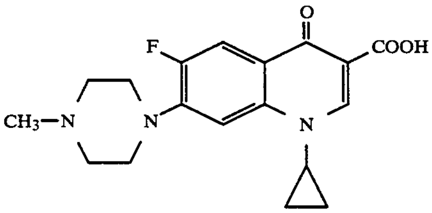 | 50 | 1 | 1 | 1 | 1 |

TABLE C-continued

Agar plate test

| Active compounds | Active compound concentration ppm | Growth in figures of rating (1 = growth, 9 = control) Microorganisms *Agrobacterium tumefaciens* | *Corynebacterium michiganense* | *Erwinia carotovora* var. *atroseptica* | *Erwinia mangiferae* |
|---|---|---|---|---|---|
| 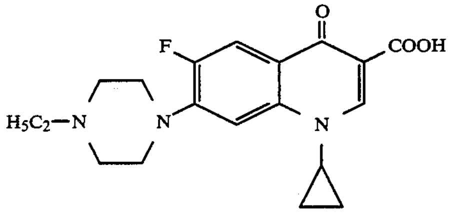 × HCl | 50 | 2 | 2 | 1 | 2 |
| 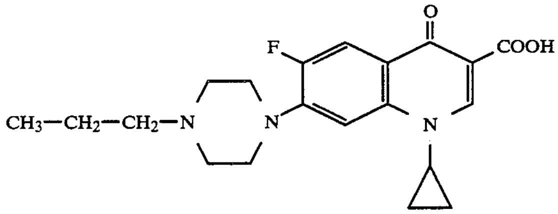 | 50 | 3 | 2 | 1 | 2 |
| 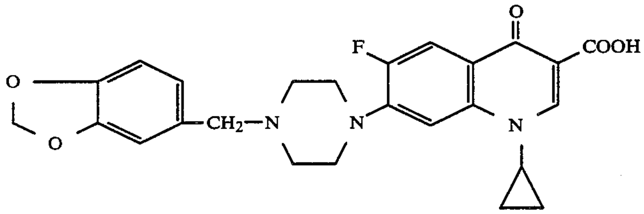 | 50 | 2 | 2 | 2 | 2 |
| 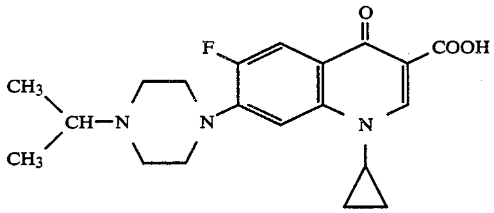 | 50 | 2 | 2 | 1 | 2 |

EXAMPLE D

Agar plate test

Nutrient medium used
15 parts by weight of agar-agar
10 parts by weight of sucrose
8 parts by weight of casein hydrolyzate
4 parts by weight of yeast extract
2 parts by weight of dipotassium hydrogen phosphate
0.3 parts by weight of magnesium phosphate
are dissolved in 1,000 ml of distilled water and the solution is kept in an autoclave at 121° C. for 15 minutes.
Solvent: 10 parts by weight of dimethylformamide
Ratio of the amounts of solvent to nutrient medium: 0.2:99.8

To produce a suitable preparation of active compound, 1 part by weight of active compound is mixed with the stated amount of solvent.

The concentrate is thoroughly mixed, in the stated proportion, with the liquid nutrient medium and the mixture is poured into Petri dishes.

When the nutrient medium has cooled and solidified, the plates are inoculated with the following microorganisms and are incubated at about 28° C.:

Evaluation is carried out after 2 days, the inhibition of growth being used as a measure of the action of the products.

The results obtained are as follows:

TABLE D
Agar plate test
| Active compounds | Active compound concentration ppm | Growth in figures of rating (1 = no growth, 9 = control) Microorganisms *Xanthomonas oryzae* | *Xanthomonas vesicatoria* | *Pseudomonas lachrymans* |
|---|---|---|---|---|
| 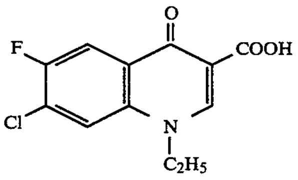 (known) | 10 | 3 | 3 | 9 |
| 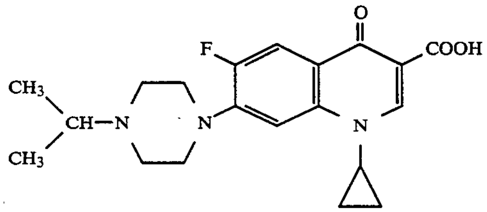 | 10 | 2 | 2 | 5 |
| 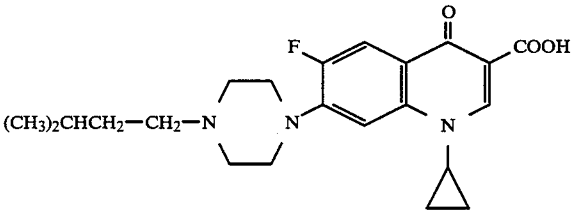 | 10 | 2 | 2 | 6 |
| 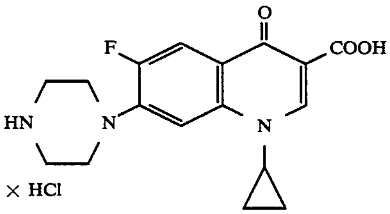 × HCl | 10 | 1 | 1 | 2 |
| 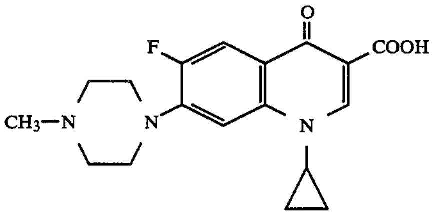 | 10 | 1 | 1 | 3 |
| 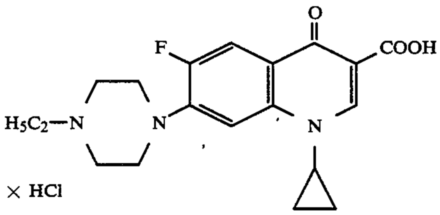 × HCl | 10 | 2 | 2 | 4 |

Preparation Examples

EXAMPLE 1

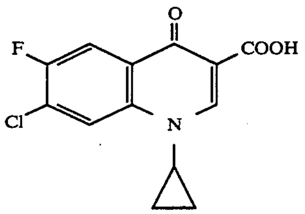

3.44 g of 80 percent strength sodium hydride are added in portions to a solution of 31.9 g of ethyl 2-(2,4-dichloro-5-fluoro-benzoyl)-3-cyclopropylaminoacrylate in 300 ml of anhydrous dioxane, while cooling with ice and stirring. The mixture is then stirred at room temperature for 30 minutes and under reflux for 2 hours and the dioxane is stripped off in vacuo. The residue (40.3 g) is suspended in 150 ml of water, 6.65 g of potassium hydroxide are added and the mixture is refluxed for 1.5 hours. The warm solution is filtered and the residue is rinsed with water. The filtrate is then acidified to pH 1-2 with half-concentrated hydrochloric acid, while cooling with ice, and the precipitate is filtered off with suction, washed with water and dried in vacuo at 100° C. 27.7 g of 7-chloro-1-cyclopropyl-6-fluoro-1,4-dihydro-4-oxo-3-quinolinecarboxylic acid of melting point 234°-237° C. are obtained in this manner.

Preparation of the starting substance 24.3 g of magnesium chips are suspended in 50 ml of anhydrous ethanol. 5 ml of carbon tetrachloride are added and, when the reaction has started, a mixture of 160 g of diethyl malonate, 100 ml of absolute ethanol and 400 ml of anhydrous ether is added dropwise, whereupon vigorous reflux is to be observed. When the reaction has subsided, the mixture is heated at the boiling point for a further 2 hours and cooled to −5° C. to −10° C. with dry ice/acetone, and a solution of 227.5 g of 2,4-dichloro-5-fluoro-benzoyl chloride in 100 ml of absolute ether is slowly added dropwise at this temperature. The mixture is stirred at 0° C. to −5° C. for 1 hour and allowed to come to room temperature overnight, and a mixture of 400 ml of ice-water and 25 ml of concentrated sulphuric acid is run in, while cooling with ice. The phases are separated and subsequently extracted twice with ether. The combined ether solutions are washed with saturated sodium chloride solution and dried with sodium sulphate and the solvent is stripped off in vacuo. 349.5 g of diethyl 2,4-dichloro-5-fluoro-benzoyl-malonate are obtained as a crude product.

0.15 g of p-toluenesulphonic acid is added to an emulsion of 34.9 g of crude diethyl 2,4-dichloro-5-fluoro-benzoyl-malonate in 50 ml of water. The mixture is heated at the boiling point for 3 hours, while stirring well, the cooled emulsion is extracted several times with methylene chloride, the combined methylene chloride solutions are washed once with saturated sodium chloride solution and dried with sodium sulphate and the solvent is distilled off in vacuo. Fractionation of the residue under a fine vacuum gives 21.8 g of ethyl 2,4-dichloro-5-fluoro-benzoylacetate of boiling point 127°-142° C./0.09 mbar.

A mixture of 21.1 g of ethyl 2,4-dichloro-5-fluoro-benzoylacetate, 16.65 g of ethyl o-formate and 18.55 g of acetic anhydride is heated at 150° C. for 2 hours. The volatile constituents are then distilled off under a water-pump vacuum and finally under a fine vacuum at a bath temperature of 120° C. 25.2 g of crude ethyl 2-(2,4-dichloro-5-benzoyl)-3-ethoxy-acrylate remain. This product is sufficiently pure for the further reactions.

4.5 g of cyclopropylamine are added dropwise to a solution of 24.9 g of ethyl(2-(2,4-dichloro-5-fluorobenzoyl)-3-ethoxy-acrylate in 80 ml of ethanol, while cooling with ice and stirring. When the exothermic reaction has subsided, stirring is continued at room temperature for 1 hour, the solvent is stripped off in vacuo and the residue is recrystallized from cyclohexane/petroleum ether. 22.9 g of ethyl 2-(2,4-dichloro-5-fluoro-benzoyl)-3-cyclopropylamino-acrylate of melting point 89°-90° C. are obtained.

The following compounds can be prepared analogously to Example 1.

2. 7-Chloro-1-cyclopropyl-6-nitro-1,4-dihydro-4-oxo-3-quinolinecarboxylic acid of melting point 265°-275° C. (decomposition)
3. 1-Cyclopropyl-6,7-difluoro-1,4-dihydro-4-oxo-3-quinolinecarboxylic acid of melting point 290° C.
4. 7-Chloro-1-cyclopropyl-1,4-dihydro-4-oxo-3-quinolinecarboxylic acid of melting point 308° C.
5. 6,7-Dichloro-1-cyclopropyl-1,4-dihydro-4-oxo-3-quinolinecarboxylic acid of melting point 265° C.

EXAMPLE 6

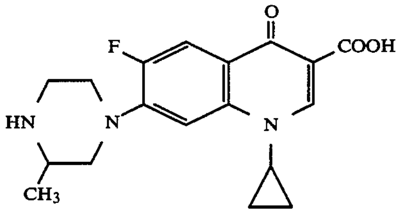

$\times \frac{1}{2} H_2O$

A mixture of 2.8 g (0.01 mol) of 7-chloro-1-cyclopropyl-6-fluoro-1,4-dihydro-4-oxo-3-quinolinecarboxylic acid and 5.1 g (0.051 mol) of 2-methylpiperazine in 6 ml of dimethylsulphoxide is heated at 140° C. for 2 hours. The solvent is then distilled off under a high vacuum, 6 ml of hot water are added to the residue and the mixture is kept at 95° C. for 1 hours. The mixture is cooled with ice and the precipitate which has separated out is filtered off with suction, washed with a little water and dissolved in a mixture of 0.8 ml of acetic acid and 10 ml of water at 90°-100° C. The filtrate is brought to pH 8 with potassium hydroxide solution (0.75 g of KOH in 0.7 ml of water), and the precipitate which has separated out is recrystallized from methanol. 1.8 g (52% of theory) of 1-cyclopropyl-6-fluoro-1,4-dihydro-4-oxo-7-(3-methyl-1-piperazinyl)-3-quinolinecarboxylic acid semihydrate of decomposition point 230°-232° C. are obtained.

EXAMPLE 7

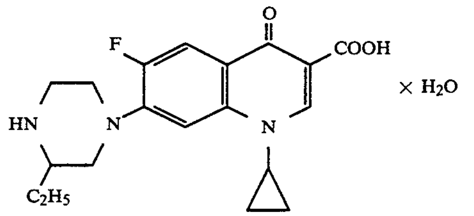

A mixture of 2.8 g (0.01 mol) of 7-chloro-1-cyclopropyl-6-fluoro-1,4-dihydro-4-oxo-3-quinolinecarboxylic acid and 3.4 g (0.03 mol) of 2-ethylpiperazine in 15 ml of dimethylsulphoxide is heated at 140° C. for 2 hours. The solution is concentrated under a high vacuum, the residue is heated to 90° C. with 30 ml of water and the precipitate which has separated out is filtered off with suction, washed with methanol and water and isolated. 1.1 g (31% of theory) of 1-cyclopropyl-6-fluoro-1,4-dihydro-4-oxo-7-(3-ethyl-1-piperazinyl)-3-quinolinecarboxylic acid monohydrate of decomposition point 255°-258° C. are obtained.

EXAMPLE 8

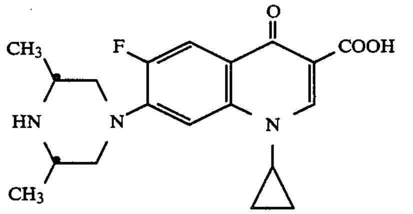

A mixture of 2.8 g (0.01 mol) of 7-chloro-1-cyclopropyl-6-fluoro-1,4-dihydro-4-oxo-3-quinolinecarboxylic acid, 1.14 g (0.01 mol) of cis-2,6-dimethylpiperazine and 2.2 g of diazabicyclo-[2,2,2]-octane is heated at 140° C. for 5 hours. The solvent is distilled off under a high vacuum, 30 ml of water are added to the residue, the suspension is adjusted to pH 8 with 2N hydrochloric acid and the precipitate which has separated out is boiled up with 30 ml of methanol. 0.75 g (21% of theory) of 1-cyclopropyl-6-fluoro-1,4-dihydro-4-oxo-7-(3,5-dimethyl-1-piperazinyl)-3-quinolinecarboxylic acid of decomposition point 234°-236° C. is obtained.

Mass spectrum: 359 ($M^+$), 290, 289 (100%, $M^+-70$), 245 and 70.

EXAMPLE 9

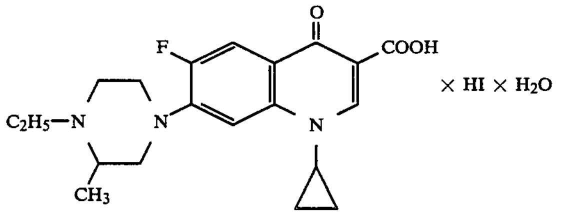

A mixture of 1.7 g (0.005 mol) of 1-cyclopropyl-6-fluoro-1,4-dihydro-4-oxo-7-(3-methyl-1-piperazinyl)-3-quinolinecarboxylic acid, 1.7 g (0.011 mol) of ethyl iodide and 1.1 g of triethylamine in 20 ml of dimethylformamide is heated at 80° C. for 3 hours. The solution is concentrated in vacuo, the crystalline residue is stirred with 10 ml of water and the undissolved product is recrystallized from methanol. 0.6 g (32% of theory) of 1-cyclopropyl-6-fluoro-1,4-dihydro-4-oxo-7-(4-ethyl-3-methyl-1-piperazinyl)-3-quinolinecarboxylic acid hydriodide monohydrate of decomposition point 285°-288° C. is obtained.

EXAMPLE 10

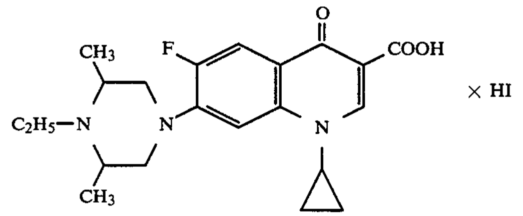

1.8 g (0.005 mol) of 1-cyclopropyl-6-fluoro-1,4-dihydro-4-oxo-7-(3,5-dimethyl-1-piperazinyl)-3-quinolinecarboxylic acid are reacted analogously to Example 9, and 0.75 g (39%) of 1-cyclopropyl-6-fluoro-1,4-dihydro-4-oxo-7-(4-ethyl-3,5-dimethyl-1-piperazinyl)-3-quinolinecarboxylic acid hydriodide of decomposition point 277°-279° C. is isolated.

The following compounds are obtained analogously to Example 9:

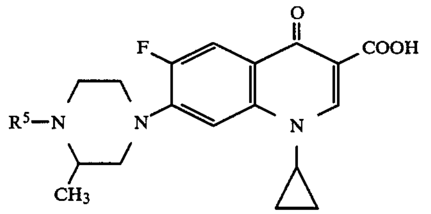

| Example | $R^5$ | Melting point [°C.] |
|---|---|---|
| 11 | $n-C_3H_7 \times HBr$ | 293-295 (decomposition) |
| 12 | $i-C_3H_7 \times HI$ | 289-291 (decomposition) |
| 13 | $i-C_4H_9$ | 198-200 |
| 14 | $n-C_5H_{11} \times HCl$ | 238-240 (decomposition) |
| 15 | $n-C_{12}H_{25} \times HCl$ | 142-145 |
| 16 | $HO-CH_2-CH_2-CH_2-$ | 198-201 (decomposition) |
| 17 | $HO-CH_2-CH_2- \times HCl$ | 240-243 (decomposition) |

EXAMPLE 18

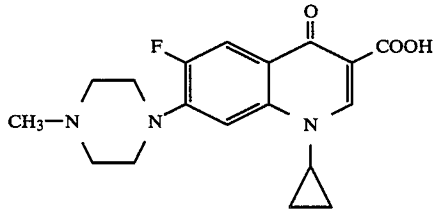

A mixture of 20 g of 7-chloro-1-cyclopropyl-6-fluoro-1,4-dihydro-4-oxo-3-quinolinecarboxylic acid, 28.5 g of N-methylpiperazine and 120 ml of anhydrous dimethylsulphoxide is heated at 135°-140° C. for 2.5 hours. The solvent is distilled off under a fine vacuum and the residue is suspended in about 50 ml of water. The solid is filtered off with suction, rinsed with water, dried over calcium chloride in a vacuum drying cabinet at 80° C. and recrystallized from glycol monomethyl ether. 14.5 g of 1-cyclopropyl-6-fluoro-1,4-dihydro-4-oxo-7-(4-methyl-1-piperazinyl)-3-quinolinecarboxylic acid of decomposition point 248°-250° C. are obtained.

EXAMPLE 19

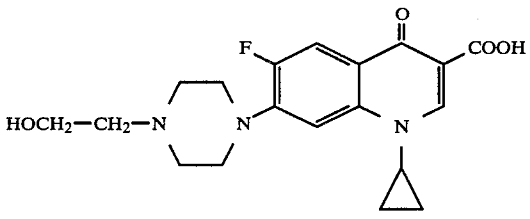

A suspension of 2.81 g of 7-chloro-1-cyclopropyl-6-fluoro-1,4-dihydro-4-oxo-3-quinolinecarboxylic acid and 5.2 g of N-(2-hydroxyethyl)-piperazine in 25 ml of dimethylsulphoxide is heated at 135°-140° C. for 2 hours. The solvent is distilled off under a fine vacuum, the residue is boiled up with 20 ml of water, the mixture is left to stand overnight at room temperature and the precipitate is filtered off with suction, while cooling with ice, washed with water and dried over calcium chloride in vacuo at 80° C. 2.1 g of 1-cyclopropyl-6-fluoro-1,4-dihydro-4-oxo-7-[4-(2-hydroxyethyl)-1-piperazinyl]-3-quinolinecarboxylic acid of decomposition point 237°-239° C. are obtained.

Mass spectrum m/e: 375 ($M^+$).

EXAMPLE 20

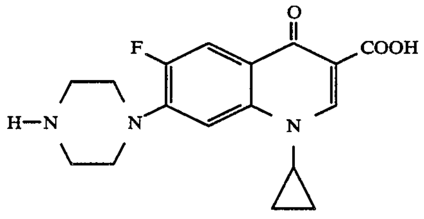

A mixture of 19.7 g of 7-chloro-1-cyclopropyl-6-fluoro-1,4-dihydro-4-oxo-3-quinolinecarboxylic acid, 30.1 g of anhydrous piperazine and 100 ml of dimethylsulphoxide is heated at 135°-140° C. for 2 hours. The solvent is distilled off under a fine vacuum, the residue is suspended in water and the solid is filtered off with suction and washed with water. For further purification, the moist crude product is boiled up with 100 ml of water and the solid is filtered off with suction at room temperature, washed with water and dried to constant weight over calcium chloride in a vacuum drying cabinet at 100° C. 19.6 g of 1-cyclopropyl-6-fluoro-1,4-dihydro-4-oxo-7-(1-piperazinyl)-3-quinolinecarboxylic acid of decomposition point 255°-257° C. are obtained.

EXAMPLE 21

1-Cyclopropyl-6-fluoro-1,4-dihydro-4-oxo-7-(1-piperazinyl)-3-quinolinecarboxylic acid hydrochloride The compound prepared by the above example is dissolved in 50 ml of hot 10 percent strength hydrochloric acid. 150 ml of ethanol are added to the filtered solution, the mixture is cooled with ice and the solid is filtered off with suction, washed with alcohol and dried in vacuo at 100° C. 18.5 g of 1-cyclopropyl-6-fluoro-1,4-dihydro-4-oxo-7-(1-piperazinyl)-3-quinolinecarboxylic acid hydrochloride are obtained as colorless crystals of decomposition point 308°-310° C.

EXAMPLE 22

Sodium 1-cyclopropyl-6-fluoro-1,4-dihydro-4-oxo-7-(1-piperazinyl)-3-quinolinecarboxylate 68 g of powdered 1-cyclopropyl-6-fluoro-1,4-dihydro-4-oxo-7-(1-piperazinyl)-3-quinolinecarboxylic acid are suspended in 300 ml of water. A solution of 7.7 g of sodium hydroxide in 30 ml of water is added and the mixture is stirred at room temperature for 30 minutes, whereupon most of the carboxylic acid dissolves. The undissolved product is filtered off and rinsed with water and the filtrate is concentrated in vacuo. The yellowish crystalline residue is dried in vacuo at 100° C. Yield: 73.4 g of the sodium salt. Melting point 325° C.

The following compounds of the general formula I can be prepared according to Examples 18-20:

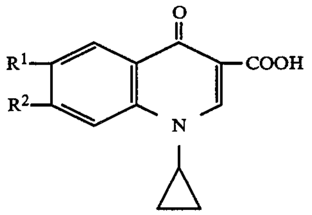

(I)

| Example No. | $R^1$ | $R^2$ | Melting point (°C.) |
|---|---|---|---|
| 23 | F | 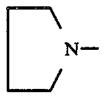 | 323 (decomposition) |
| 24 | H | 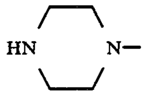 | 300 (decomposition) |

-continued
(I)
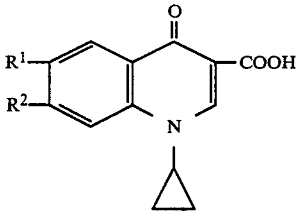
| Example No. | $R^1$ | $R^2$ | Melting point (°C.) |
|---|---|---|---|
| 25 | H | 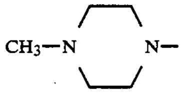 × HCl | 320 (decomposition) |
| 26 | H | 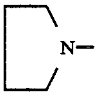 | >325 |
| 27 | F | 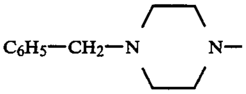 | 240 |
| 28 | F | 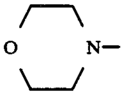 | 290 (decomposition) |
| 29 | F | 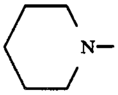 | 248 |
| 30 | F | 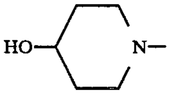 | 239 |
| 31 | F | 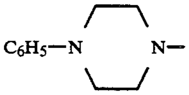 | 251 |
| 32 | F | 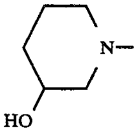 | 254 |
| 33 | Cl | 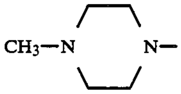 | 270 (decomposition) |
| 34 | $NO_2$ | 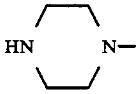 | 304 (decomposition) |
| 35 | $NO_2$ | 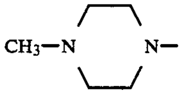 | 260 (decomposition) |

-continued
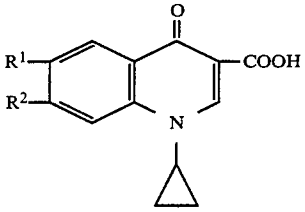
(I)
| Example No. | $R^1$ | $R^2$ | Melting point (°C.) |
|---|---|---|---|
| 36 | $NO_2$ | 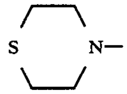 | 231 |
| 37 | F | 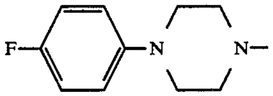 | 258 |
| 38 | F | 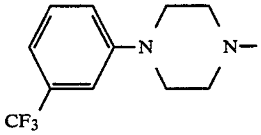 | 266 |
| 39 | F | 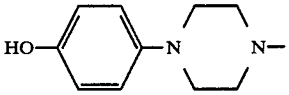 | 269 (decomposition) |
| 40 | F | 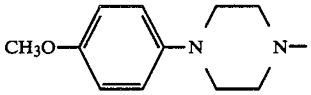 | 259 |
| 41 | F | 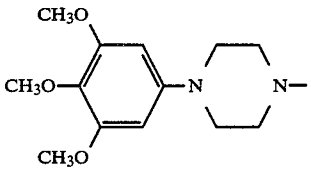 | 258 (decomposition) |
| 42 | F | 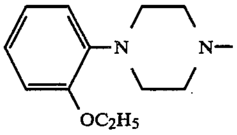 | 189 |
| 43 | F | 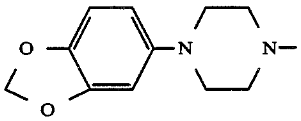 | 270 (decomposition) |
| 44 | F | 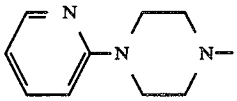 | 243 |
| 45 | F | 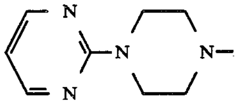 | 295 |

-continued
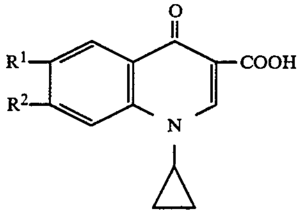
(I)
| Example No. | $R^1$ | $R^2$ | Melting point (°C.) |
|---|---|---|---|
| 46 | F | 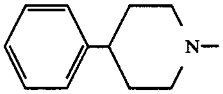 | 207 |
| 47 | F | 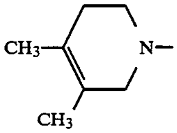 | 222 |
| 48 | F | 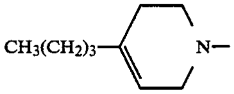 | 200 |
| 49 | F | 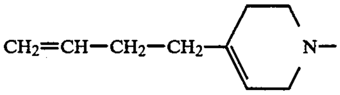 | 162 |
| 50 | F | 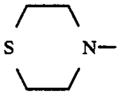 | 256 |
| 51 | F | 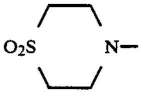 | 232 |
| 52 | F | 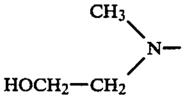 | 248 |
| 53 | F | 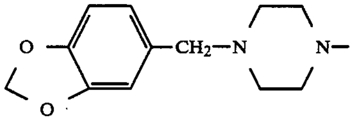 | 232 |
| 54 | F | 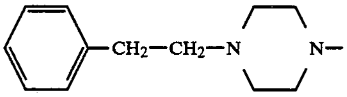 | 215 |
| 55 | F | 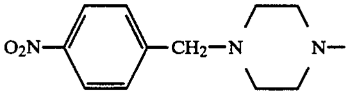 × HBr | 257 (decomposition) |

EXAMPLE 56

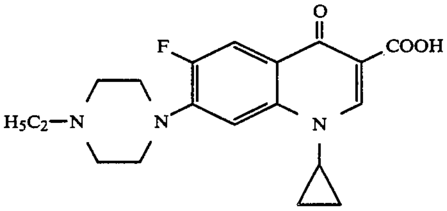 × HI

A mixture of 1.2 g of 1-cyclopropyl-6-fluoro-1,4-dihydro-4-oxo-7-(1-piperazinyl)-3-quinolinecarboxylic acid, 1.13 g of ethyl iodide, 0.73 g of triethylamine and 20 ml of N,N-dimethylformamide is heated at 70°-80° C. for 2.5 hours. The solvent is distilled off in vacuo and the residue is suspended in water. The solid is filtered off with suction, rinsed with water and pressed off on clay. 1.15 g of 1-cyclopropyl-6-fluoro-7-(4-ethyl-1-piperazinyl)-1,4-dihydro-4-oxo-3-quinolinecarboxylic acid hydriodide of decomposition point 306° C. are obtained.

Mass spectrum m/e: 359 (M+).

EXAMPLE 57

Betaine 4.9 g of the compound from Example 56 are suspended in 35 ml of water. A solution of 0.86 g of sodium bicarbonate in 10 ml of water is added and the mixture is stirred at room temperature for 1 hour. The solid is then filtered off with suction, washed with 100 ml of water and dried at 100° C. in vacuo. Yield: 4.4 g of betaine of melting point 205° C.

EXAMPLE 58

Hydrochloride of Example 56

4.4 g of betaine are briefly heated to 100° C. with 10 ml of half-concentrated hydrochloric acid. 30 ml of ethanol are added to the still warm suspension of the hydrochloride, the suspension is cooled with ice and the solid is filtered off with suction, rinsed thoroughly with ethanol and dried at 100° C. in vacuo.

Yield: 4.5 g of hydrochloride of decomposition point 328° C.

The following compounds of the general formula I can be prepared according to Examples 56 to 58:

| Example No. | $R^1$ | $R^2$ | Melting point (°C.) |
|---|---|---|---|
| 59 | F | 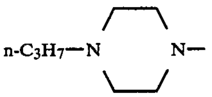 | 206 |
| 60 | F | 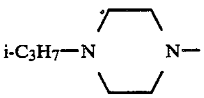 (a) (b) × HI | 222-226 (decomposition)<br>291 (decomposition) |
| 61 | F | 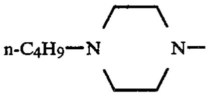 × HBr | 182 |
| 62 | F | 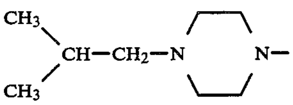 × HCl | 244 (decomposition) |
| 63 | F | 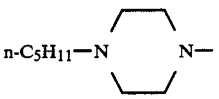 | 179 |
| 64 | F | 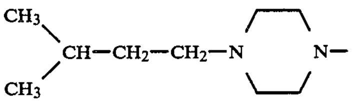 × HCl | 201 (decomposition) |
| 65 | F | 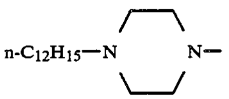 × HCl | 163 |
| 66 | F | 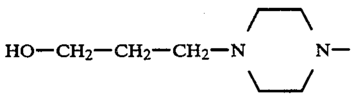 × HI | 291 (decomposition) |

-continued

| Example No. | $R^1$ | $R^2$ | Melting point (°C.) |
|---|---|---|---|
| 67 | F | 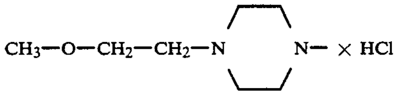 | 250 (decomposition) |

EXAMPLE 68

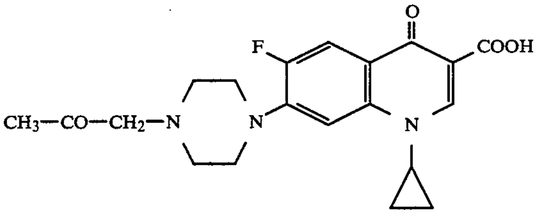

A mixture of 23.2 g (0.07 mol) of 1-cyclopropyl-6-fluoro-1,4-dihydro-4-oxo-7-(1-piperazinyl)-3-quinolinecarboxylic acid and 9.8 g of chloroacetone is heated at 80° C. in 350 ml of dimethylformamide with 14.7 g of triethylamine for 3 hours. The mixture is concentrated under a high vacuum, the residue is stirred with 140 ml of water and the undissolved solid is recrystallized from glycol monomethyl ether. Yield: 17 g (62.8% of theory) of 1-cyclopropyl-6-fluoro-1,4-dihydro-4-oxo-7-[4-(2-oxopropyl)-1-piperazinyl]-3-quinolinecarboxylic acid of decomposition point 220°-225° C.

The following compounds are prepared analogously to Example 68:

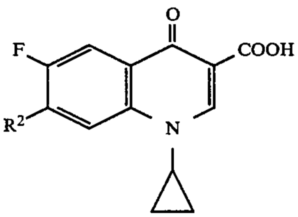

| Example | $R^2$ | Melting point [°C.] |
|---|---|---|
| 69 | 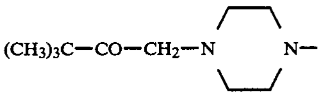 | 207-210 |
| 70 | 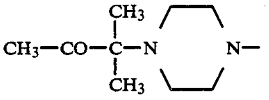 | 268-271 |
| 71 | 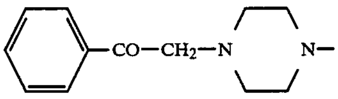 | 198-202 |
| 72 | 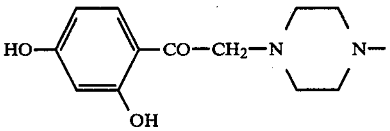 | 150-154 |
| 73 | 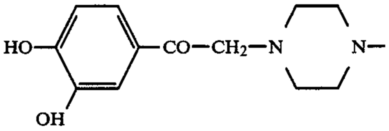 | 210-215 |

-continued

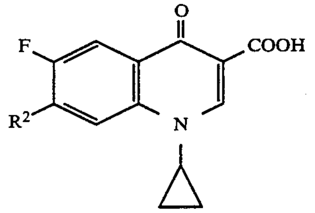

| Example | $R^2$ | Melting point [°C.] |
|---|---|---|
| 74 | 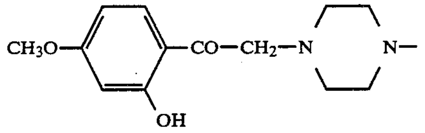 | 224–227 |
| 75 | 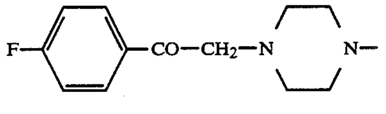 | 168–171 (decomposition) |
| 76 | 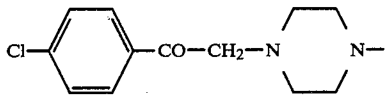 | 197–199 (decomposition) |

EXAMPLE 77

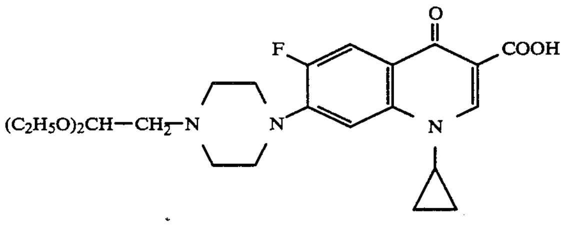

A mixture of 3.3 g (0.01 mol) of 1-cyclopropyl-6-fluoro-1,4-dihydro-4-oxo-7-(1-piperazinyl)-3-quinolinecarboxylic acid, 3.85 g (0.02 mol) of bromoacetaldehyde diethyl acetal, 2.1 g of triethylamine and 3.35 g of potassium iodide is heated at 90° C. for 11 hours. The solution is concentrated under a high vacuum, the residue is stirred with 20 ml of methanol and the precipitate which has separated out is washed several times with water and boiled up with methanol. Yield: 1.3 g (29%) of 1-cyclopropyl-7-[4-(2,2-diethoxyethyl)-1-piperazinyl]-6-fluoro-1,4-dihydro-4-oxo-3-quinolinecarboxylic acid of decomposition point 208°-212° C.

EXAMPLE 78

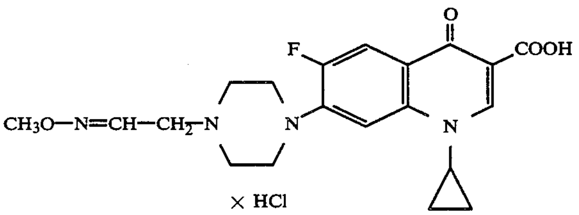

× HCl

A mixture of 3.3 g (0.01 mol) of 1-cyclopropyl-6-fluoro-1,4-dihydro-4-oxo-7-(1-piperazinyl)-3-quinolinecarboxylic acid, 1.6 g of chloroacetaldehydeoxime O-methyl ether and 2.1 g of triethylamine is stirred at 80° C. for 3 hours. It is then concentrated under a high vacuum, 30 ml of water are added and the pH is brought to 2 with 2N HCl. The precipitate is filtered off with suction, washed with water and methanol and dried under a high vacuum. Yield: 1.9 g (43% of theory) of 1-cyclopropyl-6-fluoro-1,4-dihydro-7-[4-(2-methoximinoethyl)-1-piperazinyl]-4-oxo-3-quinolinecarboxylic acid hydrochloride of decomposition point 215°-221° C.

NMR ($d_6$-dimethylsulphoxide): $\delta=3.87$ and 3.88 (2 singlets for the $CH_3O$— groups of the syn- and anti-form).

Mass spectrum: m/e 402, 371, 331, 289, 287, 245 (100%), 229, 70, 56, 44, 32, 31 and 27.

EXAMPLE 79

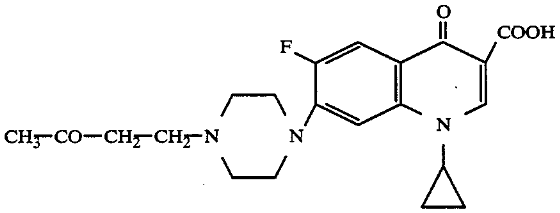

3.31 g (0.01 mol) of 1-cyclopropyl-6-fluoro-1,4-dihydro-4-oxo-7-(1-piperazinyl)-3-quinolinecarboxylic acid and 3.9 g of methyl vinyl ketone are heated under reflux in 50 ml of ethanol for 2 hours. The solid is filtered off with suction and washed with methanol to give 2.5 g (62.3% of theory) of 1-cyclopropyl-6-fluoro-1,4-dihydro-4-oxo-7-[4-(3-oxobutyl)-1-piperazinyl]-3-quinolinecarboxylic acid of decomposition point 185°-187° C.

EXAMPLE 80

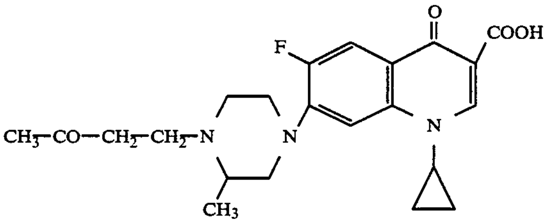

1-Cyclopropyl-6-fluoro-1,4-dihydro-7-[3-methyl-4-(3-oxobutyl)-1-piperazinyl]-4-oxo-3-quinolinecarboxylic acid (87% of theory) of decomposition point 176°-178° C. is obtained analogously to Example 79 with the starting substance from Example 6.

EXAMPLE 81

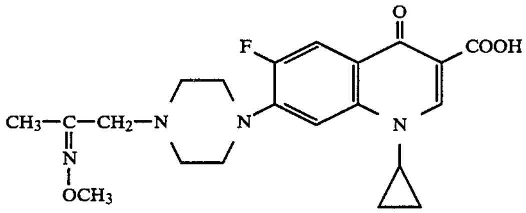

0.5 ml of concentrated hydrochloric acid is added to a mixture of 3.87 g (0.01 mol) of 1-cyclopropyl-6-fluoro-1,4-dihydro-4-oxo-7-[4-(2-oxopropyl)-1-piperazinyl]-3-quinolinecarboxylic acid and 835 mg (0.01 mol) of methoxyamine hydrochloride in 120 ml of ethanol and the mixture is heated under reflux for 3 hours. The hot solution is stirred with a little "Tonsil" (bleaching earth) and filtered. The crystals which precipitate after cooling are filtered off with suction, washed with ether and dried. Yield: 2.1 g (46% of theory) of 1-cyclopropyl-6-fluoro-1,4-dihydro-7-[4-(2-methoximinopropyl)-1-piperazinyl]-4-oxo-3-quinolinecarboxylic acid of decomposition point 215°-217° C.

The following compounds are obtained analogously to Example 81:

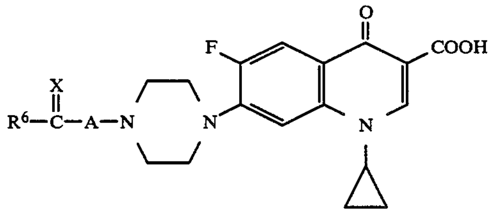

| Example | 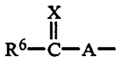 | Decomposition point |
|---|---|---|
| 82 | 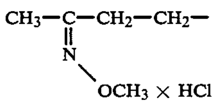 | 315-320° C. (decomposition) |

-continued

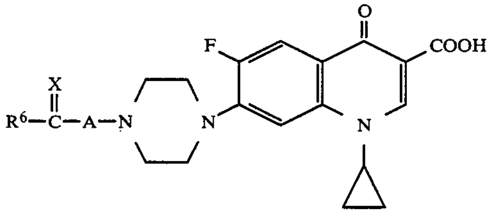

| Example | 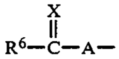 | Decomposition point |
|---|---|---|
| 83 | 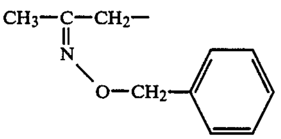 | 184-188° C. (decomposition) |
| 84 | 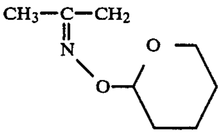 | 105-110° C. (decomposition) |
| 85 | 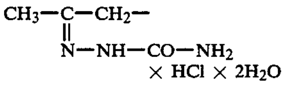 | 217-219° C. (decomposition) |
| 86 | 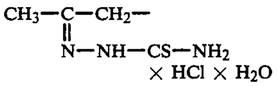 | 219-221° C. (decomposition) |

EXAMPLE 87

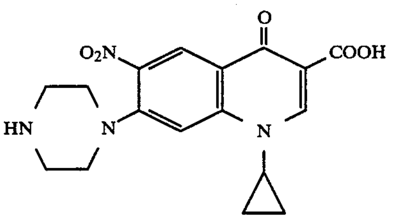

A mixture of 9.3 g (0.03 mol) of 7-chloro-1-cyclopropyl-1,4-dihydro-6-nitro-4-oxo-3-quinolinecarboxylic acid and 12.9 g (0.15 mol) of piperazine is warmed at 120° C. in 60 ml of dimethylsulphoxide for 15 minutes. After a short time, a precipitate separates out from the hot solution. The mixture is concentrated under a high vacuum, the residue is stirred with 30 ml of water and the mixture is heated again at 95° C. for 30 minutes. The mixture is brought to pH 8 with 2N hydrochloric acid, and the precipitate is filtered off with suction and washed with water and methanol. 5.8 g (54% of theory) of 1-cyclopropyl-1,4-dihydro-6-nitro-4-oxo-7-(1-piperazinyl)-3-quinolinecarboxylic acid of decomposition point 296°-298° C. are isolated.

EXAMPLE 88

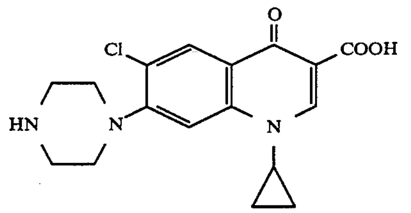

6,7 -Dichloro-1-cyclopropyl-1,4-dihydro-4-oxo-3-quinolinecarboxylic acid are converted into 1-cyclopropyl-6-chloro-1,4-dihydro-4-oxo-7-(1-piperazinyl)-3-quinolinecarboxylic acid of decomposition point 295°-298° C. analogously to Example 87.

EXAMPLE 89

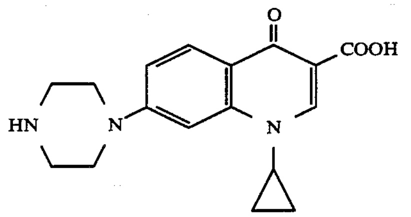

7-Chloro-1-cyclopropyl-1,4-dihydro-4-oxo-3-quinolinecarboxylic acid are reacted with piperazine to give 1-cyclopropyl-1,4-dihydro-4-oxo-7-(1-piperazinyl)-3-quinolinecarboxylic acid of decomposition point 298°-300° C. analogously to Example 87.

It will be appreciated that the instant specification and examples are set forth by way of illustration and not limitation, and that various modifications and changes may be made without departing from the spirit and scope of the present invention.

We claim:

1. A method of combating a plant fungus on plants or parts thereof which comprises applying to the fungus an effective amount for combating said fungus of a 1-cyclopropyl-1,4-dihydro-4-oxo-quinolinecarboxylic acid of the formula

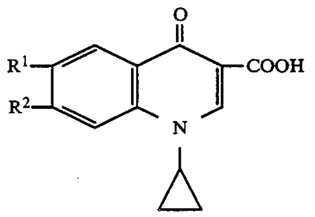

in which $R^1$ is hydrogen, fluorine, chlorine, bromine or nitro, $R^2$ is hydrogen, chlorine, fluorine or the group

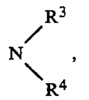

$R^3$ and $R^4$ each independently is alkyl or hydroxyalkyl which has 1 to 4 carbon atoms, or $R^3$ and $R^4$, together with the nitrogen atom on which they are positioned, form a 5-membered or 6-membered saturated or partially unsaturated heterocyclic ring which can optionally contain in its ring oxygen, sulphur or an SO, $SO_2$ or $NR^5$ group and which is optionally substituted by at least one member selected from the group consisting of alkyl with 1 to 6 carbon atoms, alkenyl with 2 to 6 carbon atoms, phenyl and hydroxyl, $R^5$ is hydrogen, alkyl which has 1 to 12 carbon atoms and is optionally substituted by hydroxyl and alkoxy with 1 to 4 carbon atoms, or is phenylalkyl which has 1 to 3 carbon atoms in the alkyl part and is optionally substituted by nitro, amino or the group $—O—CH_2—O—$, or is phenyl which is optionally substituted by at least one member selected from the group consisting of halogen, halogenoalkyl with 1 or 2 carbon atoms and with up to 5 halogen atoms, hydroxy, alkoxy with 1 to 3 carbon atoms, the group $—O—CH_2—O—$, pyridyl, pyrimidinyl and the grouping

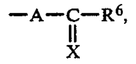

A is an optionally substituted alkylene chain with 1 to 4 carbon atoms, $R^6$ is hydrogen, alkyl with 1 to 6 carbon atoms, or phenyl which is optionally substituted by at least one member selected from the group consisting of hydroxyl, methoxy and halogen, X is oxygen or the groupings $=NOR'$, $=N—NH—R''$ or $(OR''')_2$, R' is hydrogen, alkyl with 1 to 6 carbon atoms, cycloalkyl with 5 or 6 carbon atoms, benzyl, chlorobenzyl or tetrahydropyranyl, R'' is methyl, phenyl, carbamoyl or thiocarbamoyl, and R''' is methyl or ethyl, or $(OR''')_2$ represents

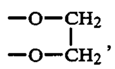

or an acid addition, alkali metal, alkaline earth metal or heavy metal salt thereof which is tolerated by plants, or a hydrate thereof.

2. The method according to claim 1, in which $R^1$ is hydrogen, fluorine, chlorine or nitro, $R^2$ is chlorine, fluorine or the group

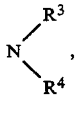

$R^3$ and $R^4$ each independently is alkyl with 1 to 3 carbon atoms or alkyl which has 2 or 3 carbon atoms and is monosubstituted by hydroxy, or $R^3$ and $R^4$, together with the nitrogen atom on which they are positioned, are pyrrolidinyl, piperidine, tetrahydropyridyl, morpholinyl, thiomorpholinyl, 1,1-dioxo-4-thiomorpholinyl or $R^5$-piperazinyl, each of which is optionally mono-, di- or tri-substituted by at least one member selected from the group consisting of alkyl with 1 to 4 carbon atoms, phenyl and hydroxyl, $R^5$ is hydrogen, alkyl with 1 to 12 carbon atoms, alkyl which has 1 to 4 carbon atoms and is monosubstituted by hydroxyl, alkyl which has 1 to 4 carbon atoms and is monosubstituted by methoxy, phenyl which is optionally mono-, di- or tri-substituted by hydroxyl, alkoxy with 1 or 2 carbon atoms, trifluoromethyl, fluorine or dioxymethylene, pyridyl, pyrimidinyl, phenalkyl which has 1 or 2 carbon atoms in the alkyl part and is optionally substituted by dioxymethylene, or the grouping

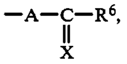

A is an alkylene chain with 1 to 3 carbon atoms, $R^6$ is hydrogen, alkyl with 1 to 4 carbon atoms, or phenyl which is optionally mono-, di, or tri-substituted by at least one of hydroxyl, fluorine, chlorine or methoxy, X is oxygen or the grouping =NOR', =N—NHR" or $(OR''')_2$, R' is alkyl with 1 to 3 carbon atoms, benzyl or tetrahydropyranyl, R" is methyl, ethyl, carbamoyl or thiocarbamoyl, and R''' methyl, or $(OR''')_2$ is

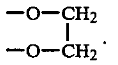

3. The method according to claim 1, wherein such compound is 1-cyclopropyl-6-fluoro-1,4-dihydro-4-oxo-7-(4-methyl-1-piperazinyl)-3-quinolinecarboxylic acid of the formula

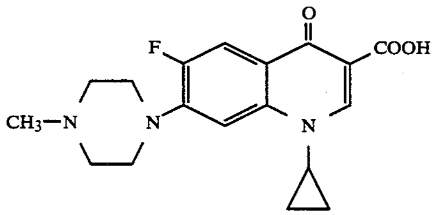

or an acid addition, alkali metal, alkaline earth metal or heavy metal salt thereof which is tolerated by plants, or a hydrate thereof.

4. The method according to claim 1, wherein such compound is 1-cyclopropyl-6-fluoro-1,4-dihydro-4-oxo-7-(1-piperazinyl)-3-quinolinecarboxylic acid of the formula

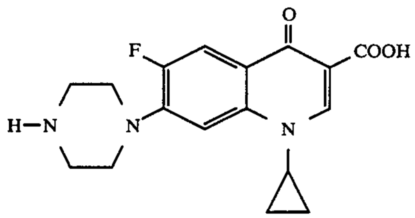

or an acid addition, alkali metal, alkaline earth metal or heavy metal salt thereof which is tolerated by plants, or a hydrate thereof.

5. The method according to claim 1, wherein such compound is 1-cyclopropyl-6-fluoro-7-(4-ethyl-1-piperazinyl)-1,4-dihydro-4-oxo-3-quinolinecarboxylic acid of the formula

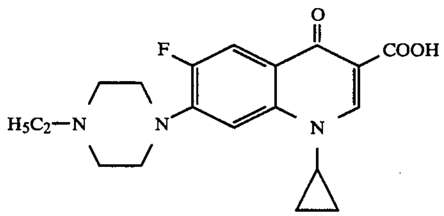

or an acid addition, alkali metal, alkaline earth metal or heavy metal salt thereof which is tolerated by plants, or a hydrate thereof.

6. The method according to claim 1, wherein such compound is 1-cyclopropyl-6-fluoro-7-(4-isopropyl-1-piperazinyl)-1,4-dihydro-4-oxo-3-quinolinecarboxylic acid of the formula

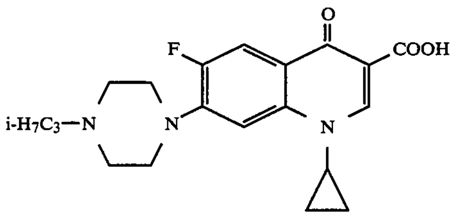

or an acid addition, alkali metal, alkaline earth metal or heavy metal salt thereof which is tolerated by plants, or a hydrate thereof.

* * * * *

UNITED STATES PATENT AND TRADEMARK OFFICE

CERTIFICATE OF CORRECTION

PATENT NO. : 4,563,459

DATED : January 7, 1986

INVENTOR(S) : Klaus Grohe, et al.

It is certified that error appears in the above-identified patent and that said Letters Patent is hereby corrected as shown below:

| | |
|---|---|
| Col. 12, line 55 and Col. 14, line 4 | Table C, 3rd line of heading, delete "1=growth" and substitute --1=no growth-- |
| Col. 38, line 22, Ex. 84 | Last column after "(decomposition)" Insert -- +) -- |
| Col. 38, line 38 | Insert -- +)solidified foam; the tetrahydropyranyl radical has partly been split off-- |
| Col. 41, line 30 | After " R'" " insert --is-- |

Signed and Sealed this

*Seventeenth* Day of *June 1986*

[SEAL]

*Attest:*

DONALD J. QUIGG

*Attesting Officer* *Commissioner of Patents and Trademarks*